(12) United States Patent
Katz et al.

(10) Patent No.: US 6,315,783 B1
(45) Date of Patent: Nov. 13, 2001

(54) SURGICAL HEAD SUPPORT

(75) Inventors: Yoav Katz, Binyamina; Hanan Katz; Arkadi Skibinsky, both of Rehovot, all of (IL)

(73) Assignee: Odin Technologies, Ltd., Yokneam Elit (IL)

( * ) Notice: Subject to any disclaimer, the term of this patent is extended or adjusted under 35 U.S.C. 154(b) by 0 days.

(21) Appl. No.: 09/545,382

(22) Filed: Apr. 7, 2000

(51) Int. Cl.$^7$ ................................................. A61B 19/00
(52) U.S. Cl. ............................................................. 606/130
(58) Field of Search .............................. 606/130; 297/391, 297/406, 407, 408, 409, 410; 600/429

(56) References Cited

U.S. PATENT DOCUMENTS

| | | | |
|---|---|---|---|
| 3,572,835 | * | 3/1971 | Kees, Jr. et al. ...................... 297/410 |
| 3,835,861 | * | 9/1974 | Kees, Jr. et al. .......................... 5/637 |
| 4,360,028 | * | 11/1982 | Barbier et al. ........................ 600/436 |
| 4,592,352 | * | 6/1986 | Patil ..................................... 606/130 |
| 5,085,219 | * | 2/1992 | Ortendahl et al. .................... 600/422 |

\* cited by examiner

*Primary Examiner*—Jeffrey A. Smith
*Assistant Examiner*—Eduardo C. Robert
(74) *Attorney, Agent, or Firm*—Pennie & Edmonds LLP (57) ABSTRACT

A surgical head support to be used for positioning and holding a patient's head during a surgical procedure in the head area. The head support includes an arcuate support having two arcuate arms, each of the arcuate arms having a free end and provided with head engaging elements for gripping the patient's head. The head support further includes a base member provided with concave semispherical recess matching a central portion of the arcuate support. The base member includes two bases adapted to slide one on top of the other perpendicular to a longitudinal axis of the arcuate support. A connecting bolt connects the arcuate support and the base member so that two positions are possible: in the first position, relative motion between the arcuate support and the base member allows rearrangement of the arcuate support with respect to the base member while defining a hemispherical plane and relative motion between the bases is allowed; in the second position, the connecting bolt firmly secures the arcuate support to the base member.

30 Claims, 6 Drawing Sheets

SURGICAL HEAD SUPPORT

THE FIELD OF THE INVENTION

This invention relates to headrests for surgical purposes. More particularly, it relates to a surgical head support for positioning and holding the head of a patient during surgery performed in the head area and craniotomies.

BACKGROUND OF THE INVENTION

Supporting and holding the head of a patient during craniotomy and other surgical operations in the head area are difficult tasks since the head is a spheroidal organ. Invasive operations in the head involve in many cases forceful acts like sawing the skull. Therefore, the need to firmly hold the head is very important On the other hand, there is also the need to move or rotate the head prior to or during the operation itself, so that the surgeon is able to perform the operation comfortably. The ease in moving or rotating the head in order to position it according to the surgical team needs is very important.

Some commercial surgical head supports are available and known in the art. A commercial head frame is manufactured by Mizuho Medical Co. LTD. The surgical head support, commercially called "Mizuho Radiolucent Head Frame", comprises a crown base on which articulations needed for the procedure can be fixed, and an enlarged head holder that renders rigidity to the crown. The head frame further comprises a table attachment for connecting the head holder to the operation table or the bed on which the patient lies The space around the patients head that this head frame occupies is relatively broad.

Ohio medical Instrument Company, Inc., manufactures a patented "Cranial Positioning System", which is disclosed in U.S. Pat. No. 3,836,861 filed in 1972. This invention provides a surgical head damp that includes two sections. One section carries a pair of head engaging pins. The second section can carry a single pin. The sections are connected by a disc and pawl arrangement, which permits rapid closure movement to bring the pins rapidly into contact with sides of the head. The pair of pins is mounted on a sliding arcuate bar, which is slidably mounted on the first section and movable to adjust for irregularities of the head and to insure proper direction of the pair of pins. The outer pin is carried by a threaded carrier, which is threaded to the second section and permits fine adjustment of the positioning of the pins. The carrier includes a spring, which urges the pin carrier thereby toward the head to provide resilient urging of the pins. The force of the spring can be varied to adjust the pressure of the clamp. This surgical head clamp has relatively large dimensions around the patient's head, and the multijoint arm that supports the head clamp also takes up a large space. Furthermore, in order to take up certain peculiar positions the multijoint arm might occupy even larger space around the patient's head.

Recently intraoperative imaging devices were introduced, offering on-line information to the surgical team and providing better operational conditions. Such is, for example, the compact MRI apparatus, described in U.S. Pat. No. 5,900,793 (Katznelson et al.), where the image acquiring means include a pair of small permanent magnets that are spaced so as to allow the insertion of the head of the patient in between them. The space within the magnets is very limited (usually in the order of 25–40 cm) and this greatly limits the size of a surgical head support that can be used for holding the patient's head during surgery.

Prior art and other standard head holders or clamps that engage relatively large space around the patients head do not allow the head to be positioned between the two magnets of the portable MRI. Moreover, the patient's head cannot be maneuvered easily in order to reposition the head in a better position relative to the surgeon or to additional medical devices that are sometimes needed in the course of operation.

There is a distinct need for a surgical head support that is confined to the near vicinity of the patient's head. In order to provide better operation conditions for the surgeon and a simple way to position and support the head, there is also a need for a good leverage system. The head holder itself has to match and firmly hold a patient's head also catering for abnormalities in head sizes or shape.

BRIEF DESCRIPTION OF THE INVENTION

It is therefore an object of the present invention to provide a surgical head support for surgical purposes that is confined to the vicinity of the patient's head and has minimal dimensions.

It is another object of the present invention to provide a surgical head support for positioning and holding a patient's head adapted to firmly hold various head sizes or shapes.

It is yet another object of the present invention to provide a surgical head support having a leverage system that enables to position the head with respect to the surgeon or the instruments and make adjustments in the location of the head holder during the procedure.

Yet another object of the present invention is to provide a surgical head support with great maneuverability allowing a wide range of orientations.

It is thus provided a surgical head support to be used for positioning and holding a patient's head during a surgical procedure in the head area comprising;

an arcuate support having a first and a second arcuate arms, said arcuate arms provided with head engaging means for gripping the patient's head;

a base member provided with concave semispherical recess matching a central portion of said arcuate support; wherein said arcuate support and said base member are connected to each other by connecting means having two states, wherein in the first state the connecting means facilitates relative motion between said arcuate support and said base member allowing repositioning of the arcuate support with respect to the base member, and herein in the second state the connecting means firmly secures said arcuate support to said base member.

Furthermore, in accordance with another preferred embodiment of the present invention, said base member is made of two bases adapted to slide one on top of the other by moving along two bars or a fork-shaped bar, said two bars are ted between the bases, perpendicularilly to the longitudinal axis of said arcuate support.

Furthermore, in accordance with another preferred embodiment of the present invention, said connecting means comprises a bolt, said bolt passing through matching bores in the bases of said base member, and whose head is confined to an elongated void provided in said arcuate support, so that said arcuate support may be rotated about the bolt's axis, and arcuate support may also slide with respect to the base member along the path defined by the elongated slit.

Furthermore, in accordance with another preferred embodiment of the present invention, said bolt extends beyond the base member and is provided with a threaded portion on which a nut is screwed on which can lock the surgical head support in a desired position.

Furthermore, in accordance with another preferred embodiment of the present invention, said head engaging means comprises a pin provided near the free end of the first arcuate arm and two pins provided on an arcuate tiltable arm mounted on the free end of said second arcuate arm.

Furthermore, in accordance with another preferred embodiment of the present invention, said arcuate tiltable arm is pivotally connected substantially at the center between the pins to a hinge that is mounted on an extension, said extension is pivotally connected to the second arcuate arm and adapted to rotate about a vertical axis.

Furthermore, in accordance with another preferred embodiment of the present invention, said arcuate tiltable arm may rotate about a shaft provided in the hinge, laterally to said arcuate tiltable arm.

Furthermore, in accordance with another preferred embodiment of the present invention, a tightening screw is adapted to secure said arcuate tiltable arm in a desired position.

Furthermore, in accordance with another preferred embodiment of the present invention, said extension is provided with a bore, said bore is adapted to accommodate a shaft coupled to said second arcuate arm, about which said extension may rotates.

Furthermore, in accordance with another preferred embodiment of the present invention, said surgical head support is made of a diamagnetic material.

Furthermore, in accordance with another preferred embodiment of the present invention, said arcuate support is made of fiberglass.

Furthermore, in accordance with another preferred embodiment of the present invention, the end of second arcuate arm is provided with an enforcing plate.

Furthermore, in accordance with another preferred embodiment of the present invention, said enforcing plate is made of titanium.

Furthermore, in accordance with another preferred embodiment of the present invention, a leverage system connects the head support to a surgery table.

Furthermore, in accordance with another preferred embodiment of the present invention, there is provided a surgical head support to be used for positioning and holding a patients head during a surgical procedure in the head area comprising:

an arcuate support having a first and a second arcuate arms, said arcuate arms provided with head engaging means for gripping the patient's head;

a base member provided with concave semispherical recess matching a central portion of said arcuate support;

a leverage system adapted to connect said base member to a surgery table.

wherein said arcuate support and said base member are connected to each other by connecting means having two states, wherein in the first state the connecting means facilitates relative motion between said arcuate support and said base member allowing repositioning of the arcuate support with respect to the base member, and wherein in the second state the connecting means firmly secures said arcuate support to said base member, wherein said leverage system facilitates three dimensional motion of Me arcuate support Furthermore, in accordance with another preferred embodiment of the present invention, said leverage system comprises a plurality of jointed arms.

Furthermore, in accordance with another preferred embodiment of the present invention, said jointed arms are pivotally connected.

Finally, in accordance with another preferred embodiment of the present invention, said jointed arms are pivotally connected by connectors each comprising two teethed discs that when forced against each other prevent relative motion and when released allow relative motion of the arms.

DETAILED DESCRIPTION OF THE INVENTION AND THE FIGURES

The present invention provides a novel design of a surgical head support for positioning and holding the patient's head prior to and during head surgery and craniotomy. The surgical head support of the present invention has small dimensions compared to the prior art surgical head holders so that other necessary medical instruments may be brought in the vicinity of the patient s head during the operation, e.g., a portable MRI. Moreover, the surgical head support of the present invention is easy to manipulate and reposition prior to and during the operation using a leverage system, so that the patient's head may be moved according to the needs and comfort of the surgical team. The leverage system provides the head holder with the ability to move in 3D directions.

Figure 1:
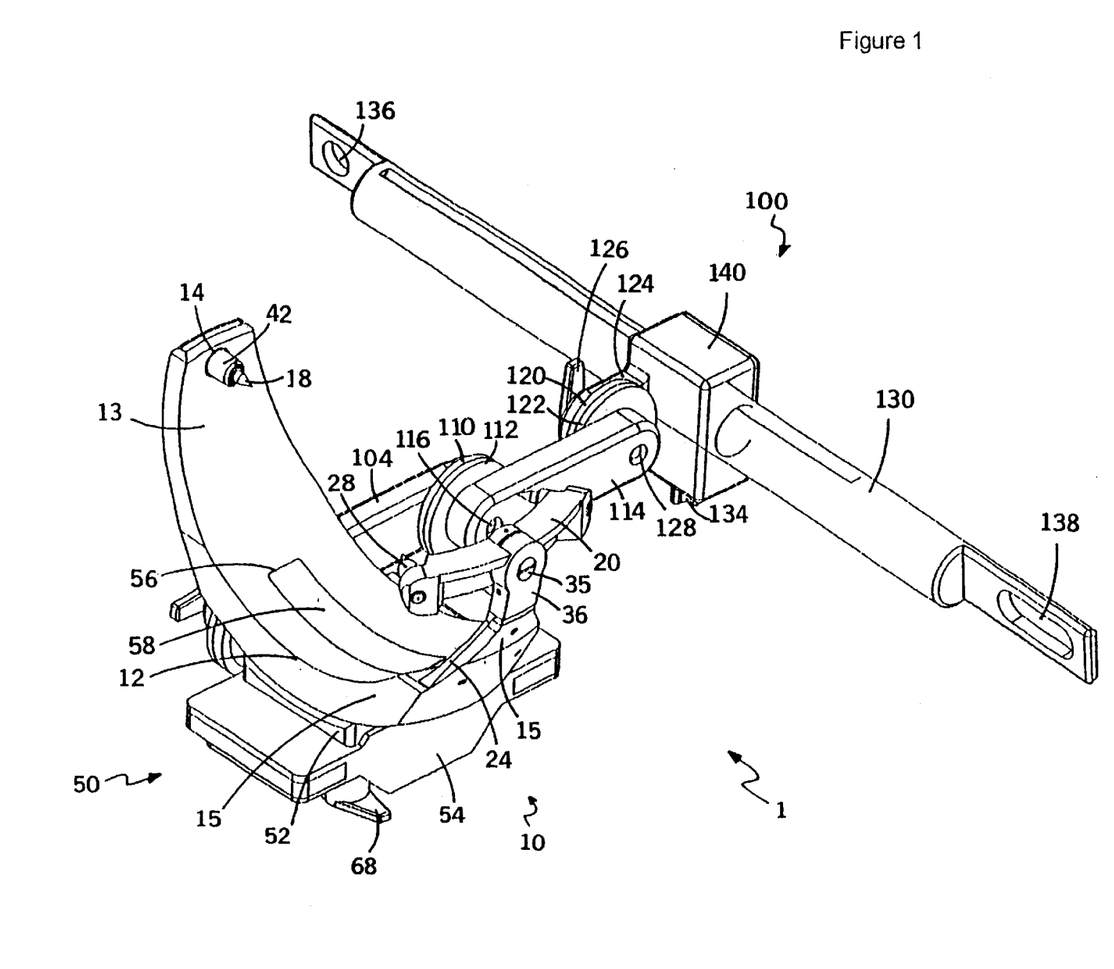
FIG. 1 illustrates an elevated isometric view of a surgical head support in accordance with a preferred embodiment of the present invention.

Reference is now made to FIG. 1 illustrating an elevated isometric view of a surgical head support in accordance with a preferred embodiment of the present invention. The surgical head support 1 comprises a head holder system 10 adapted to position and hold the patient's head, and a leverage system 100 adapted to support the head holder system and connect it to a surgery table.

Figure 5:
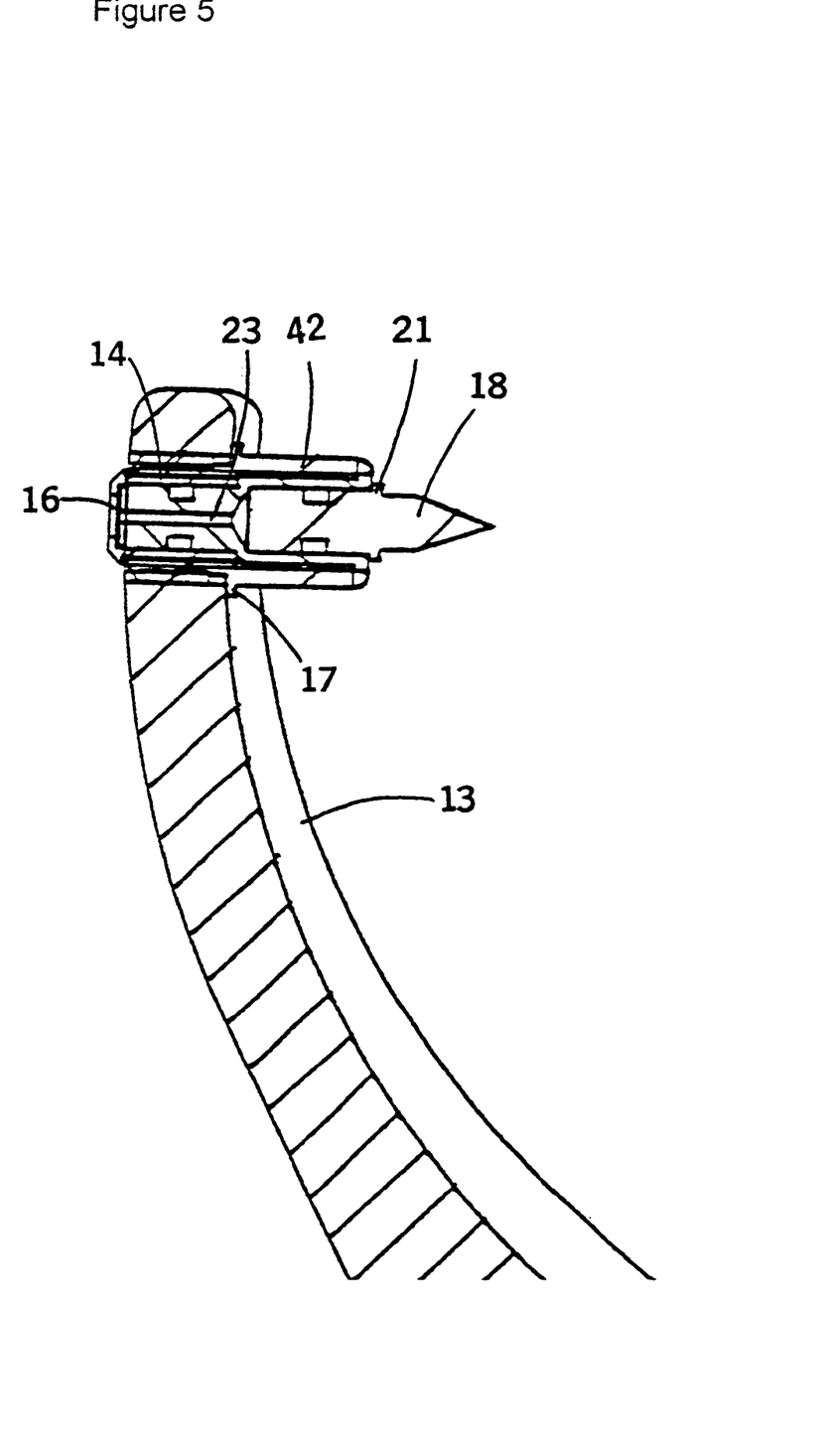
FIG. 5 illustrates a magnified side cross section across the stationary pin as shown in FIG. 3.

Head holder system 10 comprises a support 12 having two opposite arcuate arms, 13 and 15. A bore 14 designed to accommodate a stationary pin is provided near the free end of arcuate arm 13. A pin holder 16 adapted to hold a pin in the inner side of arcuate arm 13 is screwed in bore 14. Reference is now made to FIG. 5 illustrating a magnified side cross section across the stationary pin. Bore 14 is provided with an attached sleeve 42 adapted to accommodate the pin holder 16. Sleeve 42 is provided with an annular flange 17 that provide strength to the sleeve. Sleeve 42 is provided with a threaded hole 19, into which the pin holder 16 is screwed. A pin 18 is inserted in a hole 23 provided in pin holder 16. Pin 18 is also provided with an annular flange 21 that prevents the pin from being fully inserted into the threaded hole 23. In order to maintain reliable contact between pin 18 and pin holder 16, an O-ring 25 is provided. Pin 18 is designed to firmly stab the skull of the patient whose head is held by the support system. Annular flange 21 also protects pin 18 from penetrating into the skull of the patient to a depth greater that the pin's size. In order to stab the skull after positioning the head in the desire position in support 12, pin 18 is screwed outwardly from pin holder 16 and into the surface of the skull using a torque meter.

Two pins 30, 32, preferably similar to pin 18 are provided on an arcuate tiltable arm 20. Arcuate tiltable arm 20 is pivotally connected substantially at the center been pins 30, 32, to a hinge 22 that is mounted on an extension 36, which is pivotally connected to arcuate arm 15, adapted to rotate about a vertical axis. In order to render the end of arcuate arm 15 additional strength (as it is fairly thin) an enforcement in the form of a triangular plate 24 (preferably made of titanium) is screwed over it. Note that the whole, or most, of the surgical head support is made of fiberglass or other light material. If the surgical head support is to be used in conjunction with an MRI apparatus than it is to be made of diamagnetic material.

Figure 2:
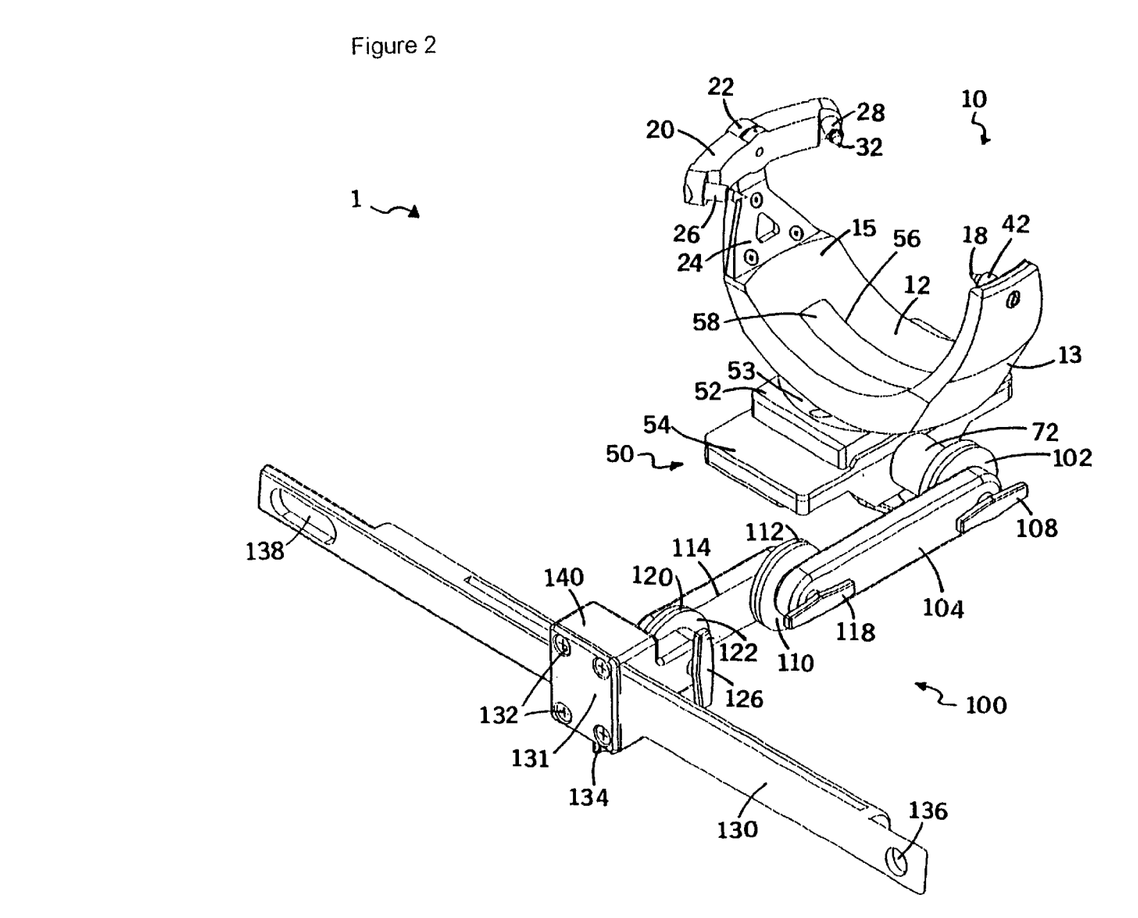
FIG. 2 illustrates another elevated isometric view of a surgical head support in accordance with a preferred embodiment of the present invention (opposite to the view of FIG. 1).

Reference is now made to FIG. 2 illustrating another elevated isometric view of a surgical head support in accordance with a preferred embodiment of the present invention. Two pin holders 26 and 28 are attached at both sides of arcuate tiltable arm 20. Pin holders 26 and 28 are provided with threaded holes into which pins 30 and 32 are screwed. Pins 30 and 32 and their holders are similar to pin 18 and its holder, all three pins are designed to firmly stab the skull of the patient after positioning the head in support 12. The pins have to be sterile before use, therefore they are removable. New and sterile pins are screwed into the corresponding threaded holes before the surgical procedure begins.

As mentioned herein, the tiltable arcuate arm is adapted to adjust the head holder system to the specific patient head size and shape and, if necessary, to slightly change the position of his head during the operation according to the needs and comfort of the surgical team. The tiltable arcuate arm also helps to adjust the head holder system to irregular head shapes or to irregularities in the head.

Figure 6:
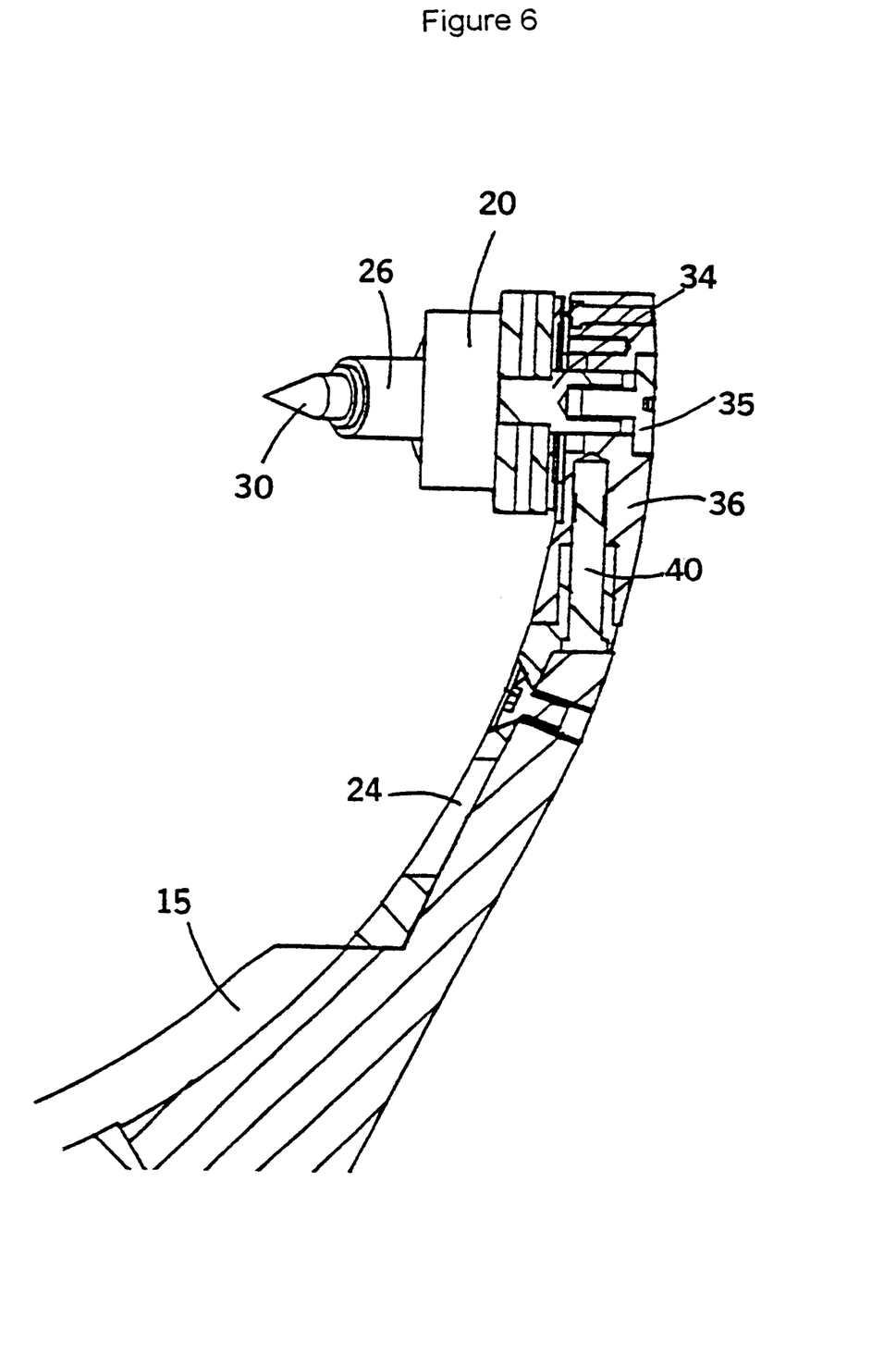
FIG. 6 illustrates a magnified side cross section across the hinge shown in FIG. 3.

Reference is now made to FIG. 6 illustrating a magnified side cross section across hinge 22. Arcuate tiltable arm 20 may rotate about a shaft 34 provided in hinge 22 laterally to arcuate tiltable arm 20. A tightening screw 35 is adapted to secure arcuate tillable arm 20 in a certain angle with respect to the patient's head.

Extension 36 is provided with a bore 38 that is adapted to accommodate a shaft 40. Extension 36 rotates about shaft 40 so that arcuate tiltable arm 20 may rotate about an additional axis that is perpendicular to the rotation axis discussed earlier. Using both rotational axes of arcuate tiltable arm 20, about shaft 34 and about shaft 40, the surgical team is able to match the pins to any type of head shape or to irregularities in the head and to slightly modify the position of the patients head according to the comfort of the surgeon and the needs of the procedure.

Returning to FIGS. 1 and 2, support 12 is mounted on a supporting assembly 50 adapted to support the patients head and to provide rotational and linear movements to support 12 Supporting assembly 50 comprises two base members 52 and 54. The upper surface of base member 52 is provided with a concave semispherical recess 53 that matches the arched outer surface of support 12 that is mounted on it. Support 12 is provided with an elongated slit 56 covered by a curved plate 58. Curved plate 58 may be removed for maintenance purposes. The slit accommodates the head of a bolt which secures support 12 to the base members as explained herein with reference to FIG. 3.

Figure 3:
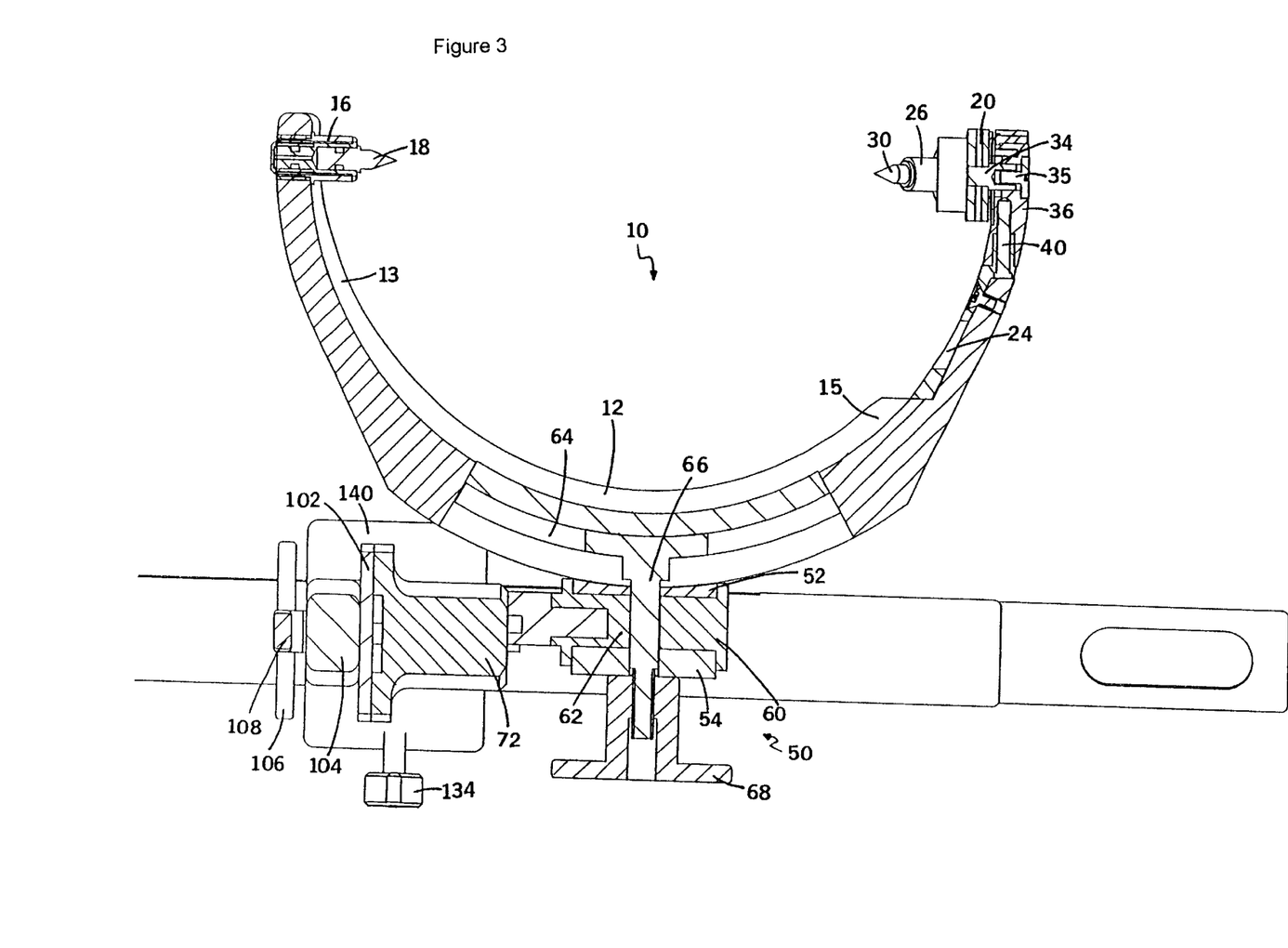
FIG. 3 illustrates a side cross section through the head holder of the surgical head support of FIG. 1.

Reference is now made to FIG. 3 that illustrates a side cross section of a surgical head support in accordance with a preferred embodiment of the present invention. Base members 52 and 54 are adapted to slide one on top of the other by moving along a bars 60 that is located between the base members and perpendicular to the longitudinal axis of support 12. The linear movement of base member 52 enables support 12, which is mounted on base member 52, to slide linearly with respect to base member 54, perpendicularly to the longitudinal axis of the arm.

Figure 4:
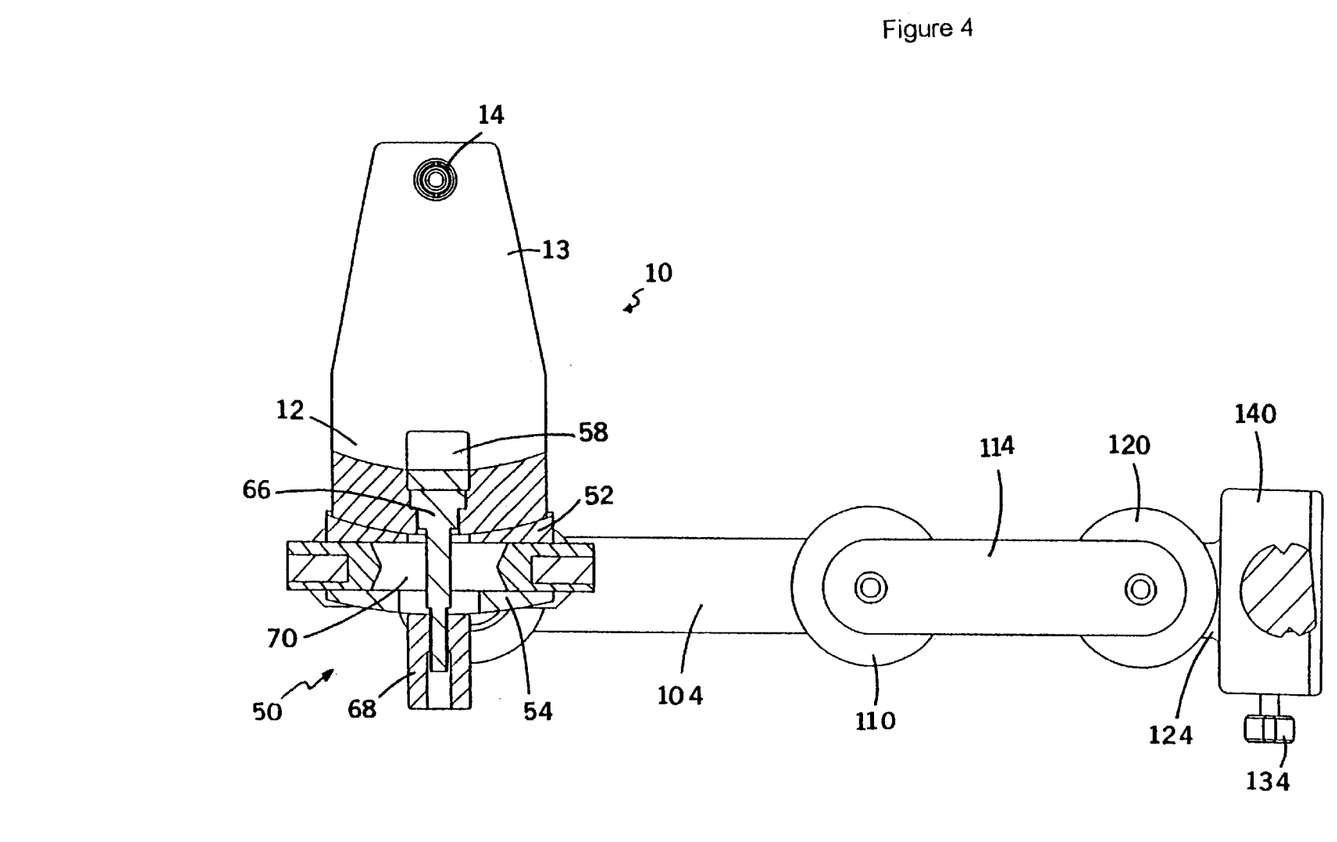
FIG. 4 illustrates a lateral cross section through the head holder of the surgical head support of FIG. 1.

Support 12 is adapted also to move along a spheroid surface about its center. Therefore, support 12 is provided with a void 64 beneath curved plate 58, adapted to accommodate the head of a bolt 66. The rod of bolt 66 passes through matching bores in base members 52 and 54 while a threaded portion of the bolts rod extends beyond base member 54. A nut 68 that matches the threaded portion of bolt 66 secures support 12 and both base members 52 and 54 together. This allows both angular and spheroidal movements maintaining a constant spheroidal volume. When nut 68 Is not firmly secured, support 12 may be rotated about the bolt's axis, and also slide with respect to the bases along the path defined by the void 64. When the patients head is positioned and no further adjustments are died, nut 68 is firmly secured. Base members 52 and 54 are provided with void 70 (shown in FIG. 4) around the unthreaded portion of bolt 66 so that the bolt may freely rotate about its axis. The linear and rotational movements of support 12 with respect to base members 52 and 54 enable the surgical team to reposition the patient's head during the operation, if needed, and secure the newly acquired position by one twist of nut 68.

Returning to FIG. 2, a connector 72 connects base member 54 to leverage system 100. Since base member 54 is a part of the assembly that supports head holder system 10, connector 72 connects head holder system 10 to leverage system 100 that is designated to secure the surgical head support of the present invention to a surgery table.

Connector 72 has an annular dilated disc that is provided on its free surface with sectoral teeth and is pivotally connected to a similar disc with sectoral teeth 102 of similar diameter. The surface of disc 102 has sectoral teeth similar to those provided on disc 72 so that when both teethed surfaces are placed adjacent to each other and forced against each other, they are prevented from relative movements.

Connector 72 is a cylinder that is allowed to rotate about its longitudinal axis so that the attached head holder system 100 may rotate in a large range about the longitudinal axis of support 12. This rotational movement may provide the surgical team with the capability to work comfortably also on the back of the patient's head when the patient is lying on his stomach. When this is the desired position for the operation, an additional support (not shown in the drawings) is provided. This support is preferably designed as a facemask allowing the patient to breathe freely with or without medical support.

A first lever arm 104 is pivotally connected at one side to disc 102 by a pivot pin 106 (shown in FIG. 3). A nut 108 secures pivot pin 106 so that the first lever arm 104 is fixed in a desired angle with respect to the longitudinal axis of connector 72. Nut 108 secures also disc 102 and the annular broadening of connector 72 from undesired relative movements between them.

The other side of first lever arm 104 is pivotally connected to disc 110 and disc 112 having their teethed surfaces adjacent to each other. One side of a second lever arm 114 is pivotally connected on the other side of discs 110 and 112 in a sandwich-like manner. A pivot pin 116 (shown in FIG.

1) passes through bores drilled in both first and second lever arms 104 and 114 and the center of both discs 110 and 112. A nut 118 secures pivot pin 116.

The other side of second lever arm 114 Is pivotally connected to another set of discs 120 and 122 that are pivotally connected to an arm 124 in the same sandwich-like manner. A nut 126 secures pivot pin 128 that passes through a bore drilled in second lever arm 114, arm 124 and both discs 120 and 122. The movements of the lever arms relative to each other enables the surgical team to adjust the distance of head holder system 10 from arm 124. When both lever arms 104 and 124 are parallel to one another and aligned, the distance between head holder system 10 and arm 124 is maximal. If the lever arms are positioned in a V-shape configuration, the distance of head holder system 10 from arm 124 may be determined by the angle between the two lever arms. Moreover, the height of head holder system 10 with respect to arm 124 may also be determined according to the surgical team needs by modifying the angle between first lever arm 104 and second lever arm 114 and also between second lever arm 114 and arm 124.

Arm 124 is attached to a housing 140. A shaft 130 is slidably connected to housing 140 so that shaft 130 slides in housing 140 along the shaft's longitudinal axis. Therefore, housing 140 is provided with two opposite openings through which shaft 130 is threaded. The longitudinal axis of shaft 130 is perpendicular to the longitudinal axis of first and second lever arms 104 and 114, and of arm 124. The sliding movement of shaft 130 perpendicularly to the arms movement direction provides another axis on which head holder system 10 may be positioned. Housing 140 is provided with a plate 131 that closes an opening in the side of the housing and is secured by four screws 132. After positioning housing 140 on shaft 130, the determined position is secured by a screw 134 that is screwed through a bore provided on the side of housing 140. Screw 134 presses against shaft 130 so that the shaft is not free to slide in housing 140.

Both ends of shaft 130 are provided with bores 136 and 138 designated to secure shaft 130 to a surgery table on which the patient lies.

After the surgical team had determined the desired positioning of head holder system 10 with respect to shaft 130, all nuts are secured firmly so that there is no relative movement between he movable parts of the apparatus. A firm positioning of the surgical head support prevents movements of the head as a result of accidental shift of the patient or the medical instruments, which may be extremely hazardous.

Leverage system 100 allows three dimensional movements to head holder system 10 with respect to shaft 130. The distance of head holder system 10 from the longitudinal axis of shaft 130 may vary, the height of the head holder system with respect to the shaft may be changed and the position of head holder system 10 along the longitudinal axis of shaft 130 may vary, too. This three dimensional movement possibility of the head holder system enables the surgical team to position and support the patients head so that the surgical procedure may be accomplished in maximal comfort for the surgeon. The movement possibility of the surgical head support of the present invention provides the surgical team with the ability to position the head of the patient in the vicinity of medical assisting devil such as a portable MR magnets.

It should be clear that the description of the embodiments and attached Figures set forth in this specification serves only for a better understanding of the invention, without limiting its scope as covered by the following Claims.

It should also be clear that a person in the art, after reading the present specification could make adjustments or amendments to the attached Figures and above described embodiments that would still be covered by the following Claims.

What is claimed is:

1. A surgical head support for positioning and holding a patient's head during a surgical procedure in the head area comprising:

an arcuate support having a central portion connected to first and second arcuate arms, said first and second arcuate arms each having a free end and being provided with head engaging means for gripping the patient's head, a longitudinal axis of the arcuate support being defined as an axis passing through said free ends; and a base member provided with a concave semispherical recess matching the central portion of said arcuate support;

wherein:

said arcuate support and said base member are connected to each other by connecting means having two states, wherein in the first state the connecting means facilitates relative motion between said arcuate support and said base member allowing repositioning of the arcuate support with respect to the base member, and wherein in the second state the connecting means firmly secures said arcuate support to said base member; and said base member comprises two bases adapted to slide one on top of the other in a direction perpendicular to said longitudinal axis.

2. The surgical head support as claimed in claim 1, wherein said connecting means comprises a bolt, said bolt passing through matching bores in the bases of said base member, and whose head is confined to an elongated slit provided in said arcuate support, so that said arcuate support may be rotated about the bolt's axis, and said arcuate support may also slide with respect to the base member along a path defined by the elongated slit.

3. The surgical head support as claimed in claim 2, wherein said bolt extends beyond the base member and is provided with a threaded portion on which a nut is screwed.

4. The surgical head support as claimed in claim 1, wherein said surgical head support is made of a diamagnetic material.

5. The surgical head support as claimed in claim 1, wherein said arcuate support is made of fiberglass.

6. The surgical head support as claimed in claim 1, wherein a leverage system connects the head support to a surgery table.

7. A surgical head support for positioning and holding a patient's head during a surgical procedure in the head area comprising:

an arcuate support having a central portion connected to first and second arcuate arms, said first and second arcuate arms each having a free end and being provided with head engaging means for gripping the patient's head, a longitudinal axis of the arcuate support being defined as an axis passing through said free ends; and a base member provided with a concave semispherical recess matching the central portion of said arcuate support;

wherein:

said arcuate support and said base member are connected to each other by connecting means having two states, wherein in the first state the connecting means facilitates relative motion between said arcuate support and said base member allowing repositioning of the arcuate support with respect to the base member, and wherein in the second state the connecting means firmly secures said arcuate support to said base member; and said head engaging means comprises a pin provided near the free end of the first arcuate arm and two pins provided on an arcuate tiltable arm mounted on the free end of said second arcuate arm.

8. The surgical head support as claimed in claim 7, wherein said arcuate tiltable arm is pivotally connected substantially at a center portion between the two pins to a hinge that is mounted on an extension, said extension is pivotally connected to the second arcuate arm and adapted to rotate about a vertical axis.

9. The surgical head support as claimed in claim 8, wherein said arcuate tiltable arm may rotate about a shaft provided in the hinge, laterally to said arcuate tiltable arm.

10. The surgical head support as claimed in claim 8, wherein said extension is provided with a bore, said bore is adapted to accommodate a shaft coupled to said second arcuate arm, about which said extension may rotate.

11. The surgical head support as claimed in claim 7, wherein a tightening screw is adapted to secure said arcuate tiltable arm a desired position.

12. A surgical head support for positioning and holding a patient's head during a surgical procedure in the head area comprising:

an arcuate support having a central portion connected to first and second arcuate arms, said first and second arcuate arms each having a free end and being provided with head engaging means for gripping the patient's head, a longitudinal axis of the arcuate support being defined as an axis passing through said free ends; and a base member provided with a concave semispherical recess matching the central portion of said arcuate support;

wherein:

said arcuate support and said base member are connected to each other by connecting means having two states, wherein in the first state the connecting means facilitates relative motion between said arcuate support and said base member allowing repositioning of the arcuate support with respect to the base member, and wherein in the second state the connecting means firmly secures said arcuate support to said base member; and the free end of said second arcuate arm is provided with an enforcing plate.

13. The surgical head support as claimed in claim 12, wherein said enforcing plate is made of titanium.

14. A surgical head support to be used for positioning and holding a patient's head during a surgical procedure in the head area comprising:

an arcuate support having a first and a second arcuate arms, each of the arcuate arms having a free end, a longitudinal axis is defined as the axis passing between both free ends, said arcuate arms provided with head engaging means for gripping the patient's head, said arcuate support further provided with an elongated slit;

a base member provided with concave semispherical recess matching a central portion of said arcuate support, said base member comprises two bases adapted to slide one on top of the other, perpendicular to the longitudinal axis; and a connecting means passing through said elongated slit and connecting said arcuate support and said base member to each other, said connecting means adapted to be in two positions, wherein in the first position said connecting means is loose, facilitating relative motion between said arcuate support and said base member and allowing rearranging the arcuate support with respect to the base member while defining a hemispherical plane that slides along said elongated slit and facilitating relative motion between said bases, and wherein in the second position the connecting means is tight, firmly securing said arcuate support to said base member.

15. The surgical head support as claimed in claim 14, wherein two bars are provided between said two bases allowing said two bases to slide one on top of the other.

16. The surgical head support as claimed in claim 14, wherein said connecting means comprises a bolt, said bolt passing through matching bores in the bases of said base member, and whose head is confined in said elongated slit, so that said arcuate support may be rotated about the bolt's axis, and said arcuate support may also slide with respect to the base member along a path defined by said elongated slit.

17. The surgical head support as claimed in claim 16, wherein said bolt extends beyond the base member and is provided with a threaded portion on which a nut, which can lock the surgical head support in a desired position, is screwed.

18. The surgical head support as claimed in claim 14, wherein said head engaging means comprises a pin provided near the free end of the first arcuate arm and two pins provided on an arcuate tiltable arm mounted on the free end of said second arcuate arm.

19. The surgical head support as claimed in claim 18, wherein a tightening screw is adapted to secure said arcuate tiltable arm in a desired position.

20. The surgical head support as claimed in claim 18, wherein said arcuate tiltable arm is pivotally connected substantially at a central portion between the pins to a hinge that is mounted on an extension, said extension is pivotally connected to the second arcuate arm and adapted to rotate about a vertical axis.

21. The surgical head support as claimed in claim 20, wherein said arcuate tiltable arm may rotate about a shaft provided in the hinge, laterally to said arcuate tiltable arm.

22. The surgical head support as claimed in claim 20, wherein said extension is provided with a bore, said bore is adapted to accommodate a shaft coupled to said second arcuate arm, about which said extension may rotate.

23. The surgical head support as claimed in claim 14, wherein said surgical head support is made of a diamagnetic material.

24. The surgical head support as claimed in claim 14, wherein said arcuate support is made of fiberglass.

25. The surgical head support as claimed in claim 14, wherein the free end of the second arcuate arm is provided with an enforcing plate.

26. The surgical head support as claimed in claim 25, wherein said enforcing plate is made of titanium.

27. The surgical head support as claimed in claim 14, wherein a leverage system connects the head support to a surgery table.

28. The surgical head support as claimed in claim 27, wherein said leverage system comprises a plurality of jointed arms.

29. The surgical head support as claimed in claim 28, wherein said jointed arms are pivotally connected.

30. The surgical head support as claimed in claim 29, wherein said jointed arms are pivotally connected by connectors each comprising two teethed discs that when forced against each other prevent relative motion and when released allow relative motion of the arms.

* * * * *